United States Patent [19]

Chazan et al.

[11] 4,146,617

[45] Mar. 27, 1979

[54] DESOXYSTREPTAMINE DERIVATIVES, SALTS, PHARMACEUTICAL COMPOSITIONS AND METHOD OF USE

[75] Inventors: Jean-Bernard Chazan, Paris; Jean-Claude Gasc, Bondy, both of France

[73] Assignee: Roussel Uclaf, Romainville, France

[21] Appl. No.: 754,942

[22] Filed: Dec. 28, 1976

Related U.S. Application Data

[63] Continuation-in-part of Ser. No. 705,576, Jul. 15, 1976, abandoned.

[30] Foreign Application Priority Data

Nov. 17, 1976 [FR] France .................................. 76 34598

[51] Int. Cl.$^2$ ........................ A61K 31/71; C07H 15/22
[52] U.S. Cl. .......................................... 424/180; 536/4; 536/17
[58] Field of Search .............................. 536/17; 424/180

[56] References Cited

U.S. PATENT DOCUMENTS

| | | | |
|---|---|---|---|
| 3,781,268 | 12/1973 | Kawaguchi et al. | 536/17 |
| 3,796,699 | 3/1974 | Naito et al. | 536/17 |
| 3,959,255 | 5/1976 | Chazan et al. | 536/17 |

*Primary Examiner*—Johnnie R. Brown
*Attorney, Agent, or Firm*—Bacon & Thomas

[57] ABSTRACT

The present invention has as its objects a new derivative of the aminoglycoside family, namely $N_1$[L-(—)2-hydroxy-4-amino butyroyl]4-0[2',6'-diamino 2',6'-didesoxya, D glucopyranosyl]6-0[3"-methylamino 3",4",6"-tridesoxy α, D-xylohexopyranosyl]2-desoxy streptamine, as well as its mineral or organic acid addition salts, its process of preparation and methods of treatment using the same.

9 Claims, No Drawings

DESOXYSTREPTAMINE DERIVATIVES, SALTS, PHARMACEUTICAL COMPOSITIONS AND METHOD OF USE

THE CROSS REFERENCES TO RELATED APPLICATION

This application is a continuation-in-part of Applicants' copending application Ser. No. 705,576 filed July 15, 1976, now abandoned.

The present invention has as one of its objects a new derivative of the aminoglycoside family, namely $N_1$[L(−) 2-hydroxy 4-amino butyroyl] 4-0 [2',6'-diamino 2',6'-didesoxy α, D glucopyranosyl] 6-0 [3"-methylamino 3",4",6"-tridesoxyα, D-xylohexopyranosyl] 2-desoxy streptamine of the formula:

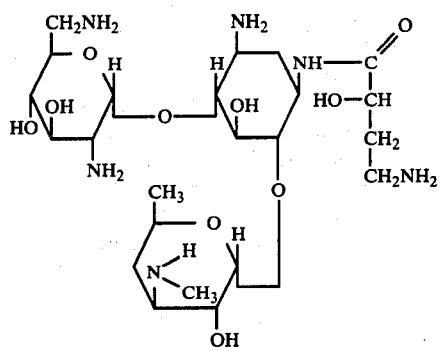

as well as its mineral or organic acid addition salts.

The above salts can be obtained by the total or partial neutralisation of the five amino functions of the product of formula I. The above salts may be pharmaceutical acceptable salts.

These salts can be, for example, a hydrochloride, a hydrobromide, a nitrate, a sulphate, a phosphate, an acetate, a formate, a benzoate, a maleate, a fumarate, a succinate, a tartrate, a citrate, an oxalate, a benzylate, a glyoxylate, an aspartate, an alkane sulphonate or an arylsulphonate.

The invention also has as one of its objects a process for preparing the product of formula I and its salts.

The process is characterised in that the product of formula:

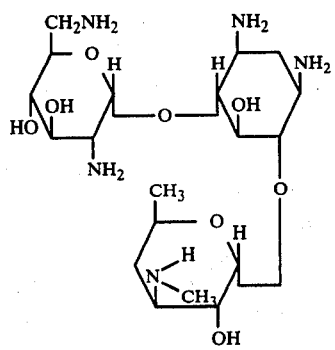

is reacted with the product of formula:

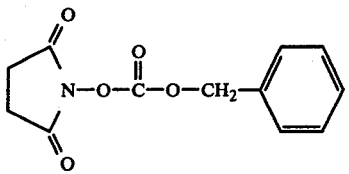

to obtain a product of the formula:

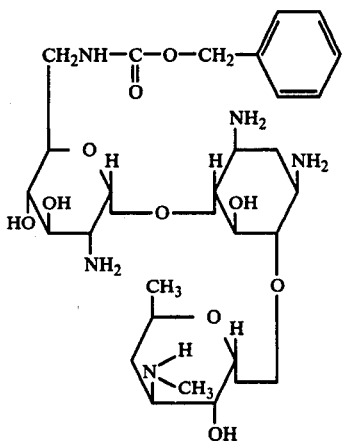

which is reacted with a product of formula:

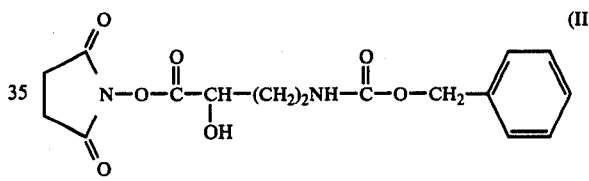

to obtain the product of formula IV:

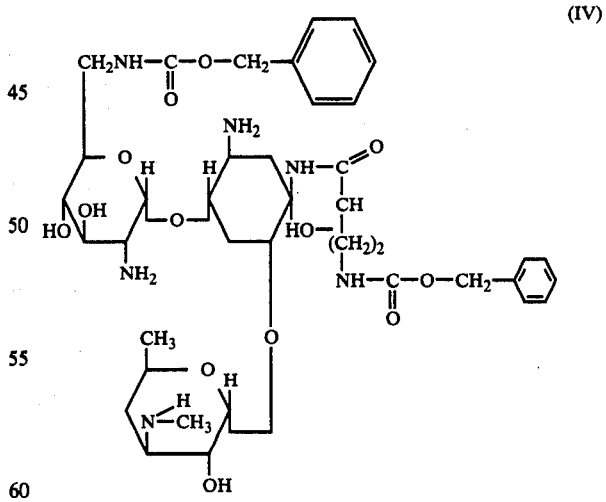

which is treated with hydrogen in the presence of a catalyst to obtain the product of formula I, which, if desired, is salified by the action of a mineral or organic acid.

In a preferred method of carrying out the above process, the product of formula II' is reacted with the product of formula II in a solvent which is a mixture of dimethyl formamide and water, but dimethyl acetamide, dioxan, tetrahydrofuran, pyridine, water, acetone, ethanol, methanol and 1,2-dimethoxy ethane can also be used, alone or in admixture.

The product of formula III' is reacted with the product of formula III, preferably using a solvent which is a mixture of water and 1,2-dimethoxy ethane, but dioxan, dimethyl acetamide, dimethyl formamide, tetrahydrofuran, the dimethyl ether of propylene glycol or water can also be used, alone or in admixture.

The conversion of the product of formula IV to the product of formula I takes place in the presence of hydrogen and a metal catalyst. The metal catalyst is preferably palladium, but platinum, Raney nickel, rhodium, nickel or ruthenium can also be used. Preferably a solvent is used, which is a mixture of water and a solvent miscible with water such as dioxan, but tetrahydrofuran, 1,2-dimethoxy ethane or the dimethyl ether of propylene glycol can also be used.

The salification of the product of formula I can be carried out by the usual methods. It can be obtained by the action on this product of acids such as, for example, hydrochloric, hydrobromic, nitric, sulphuric, phosphoric, acetic, formic, benzoic, maleic, fumaric, succinic, tartaric, citric, oxalic, benzylic, glyoxylic and aspartic acids, alkane sulphonic acids such as methane sulfonic acid and aryl sulphonic acids such as paratoluenesulfonic acid and the like. This salification is preferably carried out in a solvent or a mixture of solvents such as water, ethyl ether, methanol or acetone. The preparation of the sulfate salt is described in Example 2.

The product of formula II and its sulphate used as a starting material in the process are described in U.S. Pat. No. 3,959,255.

The product of formula I and its acid addition salts possess very interesting antibiotic activity, on the one hand against Gram-positive bacteria such as Staphylococci and especially the penicillino-resistant Staphylococci, and Streptococci, and on the other hand against Gram-negative bacteria and especially against the coliform bacteria.

These properties render the product of formula I, as well as its therapeutically compatible salts, suitable for use as medicaments, especially in the treatment of staphylococcal infections such as staphylococcal septicaemia, malignant facial staphylococcal infections, staphylococcal skin infections, pyodermatitis, septic and suppurating sores, anthrax, phlegmons, erysipelas, acute primary or post-influenza staphylococcal infections, bronchopneumonia, pulmonary suppurations and colonbacillus infections.

The product of formula I, as well as its therapeutically compatible salts, can also be used in the treatment of infections caused by Klebsiella, by Psuedomonas and by Enterobacter.

The invention extends to pharmaceutical compositions containing, as active principle, the product of formula I or one of its therapeutically compatible salts.

These pharmaceutical compositions can be administered by oral, rectal or parenteral route, or by local route by topical application to the skin and the mucous membranes.

They can be solid or liquid and can be presented in the pharmaceutical forms currently used in human medicine such as, for example, plain or sugar-coated tablets, gelatin capsules, granules, suppositories, injectable preparations, ointments, creams and gels; they are prepared according to the usual methods. The active principle or principles can be incorporated in excipients (i.e., a pharmaceutically acceptable carrier) conventionally employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and/or preservatives.

The dosage varies depending especially upon the route of administration, the complaint treated and the subject concerned.

For example, in the adult it can vary between 100 mg and 1 g per day in man by parenteral route for the product of formula I.

The invention also has as an object the method of treatment of a patient suffering from the above infections which comprises administering to the patient suffering from the infection a pharmaceutical composition as described containing the compound of formula I in an amount which is effective to relieve said infection. In the adult human being the amount of the compound of formula I administered can vary between 100 mg and 1 gram per day by parenteral route.

More specifically, the method of treatment of this invention comprises a method for the treatment of staphylococcies, streptococcies, pneumonies, and collibacillases. Also included is the treatment of infections caused by Klebsiella, by Pseudomonas and by Enterobacter by administering to a patient suffering from the infection an effective amount of the compound of formula I.

The process of the invention enables the production of new intermediate products which are especially useful for the preparation of the product of formula I. These intermediate products have the formula:

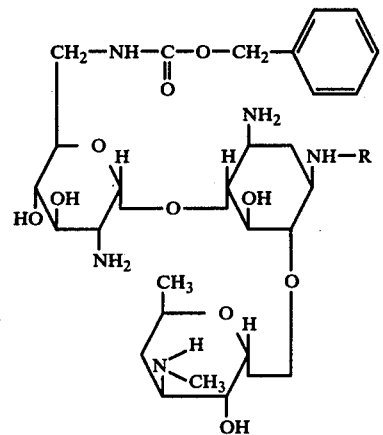

in which R represents a hydrogen atom or the radical

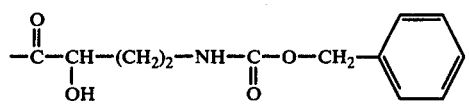

The following examples serve to illustrate the invention but in no way are to be considered limiting.

EXAMPLE 1

$N_1$[L (−) 2-hydroxy 4-amino butyroyl/ 4-0 /2',6'-diamino 2',6'-didesoxy α, D glucopyranosyl] 6-0 [3''- methylamino 3",4",6"-tridesoxy α,D xylohexopyranosyl] 2-desoxy streptamine:

Stage A: 4-0 [2'-amino 6'-benzyloxycarbonylamino 2',6'-didesoxy α, D glucopyranosyl] 6-0 [3"-methylamino 3"4"6"-tridesoxy α, D xylohexopyranosyl] 2-desoxy streptamine.

To 5.5 g of 4-0 [2',6'-diamino 2',6'-didesoxy α, D glycopyranosyl] 6-0 [3"-methylamino 3",4",6"-tridesoxy α, D xylohexopyranosyl] 2-desoxy streptamine dissolved in 58 cm³ of distilled water, there are added, at 20°-25° C., 60 cm³ of dimethyl formamide. The whole is cooled to −5° C. and 3.01 g of N'-(benzyloxycarbonyloxy) succinimide in solution in 60 cm³ of dimethyl formamide are slowly added. The whole is agitated for 20 hours at −5° C. then for 24 hours at 20°-25° C. It is evaporated to dryness and the residue taken up with water saturated with n-butanol. It is then washed with butanol saturated with water. The phases are evaporated to dryness, with the aqueous phase giving 6.21 g, and the butanol phase 2.82 g. of the product.

By chromatography on a layer of silica, with an eluant constituted by 4:4:1 chloroform, methanol and ammonia, it is established that the aqueous phase is rich in expected product. This phase is purified on an ion exchange resin of the carboxylic type in $NH^+_4$ form.

The product is fixed in an aqueous solution, then eluted with 0.1 N dilute ammonia, and 1.72 g of expected product are obtained.

Stage B: $N_1$ [L (−) 2-hydroxy 4-benzyloxycarbonylamino butyroyl/ 4-0 [2-amino 6'-benzyloxycarbonylamino 2',6'-didesoxyα, D glucopyranosyl] 6-0 [3"-methylamino 3",4",6"-tridesoxyα, D xylohexopyranosyl] 2-desoxy streptamine.

To a solution of 1.8 g of product obtained in the previous stage, in 14 cm³ of distilled water and 14 cm³ of 1,2-dimethoxyethane cooled to +5° C., there are added, over 1 hour, 1.1 g of the N-hydroxysuccinimide ester of L (−) γ benzyloxycarbonylamino α hydroxy butyric acid in a solution in 28 cm³ of dimethoxyethane.

The reaction mixture is maintained under agitation for 15 hours, between 5° and 10° C., and evaporated to dryness under vacuum. The dry extract is chromatographed on silica with an eluant consisting of 75:25:5 chloroform, methanol and ammonia.

The expected product, which has a Rf of 0.45, is characterized on silica gel, eluting with a mixture consisting of 2:2:1 methanol, chloroform and ammonia.

Stage C: $N_1$ [L (−) 2-hydroxy 4-amino butyroyl/ 4-0 /2',6'-diamino 2',6'-didesoxyα, D glucopyranosyl] 6-0 [3"-methylamino 3"4"6"-tridesoxyα, D xylohexopyranosyl] 2-desoxy streptamine.

To the solution of 473 mg of the product obtained in the previous stage in 6 cm³ of distilled water, 6 cm³ of dioxan and 0.15 cm³ of acetic acid; there are added, at 20°-25° C., 90 mg of catalyst containing 10% of palladium on charcoal. Hydrogen is bubbled-in. After 5 hours' reaction, 30 mg of catalyst are added. After 1 further hour's bubbling-in of hydrogen, the agitation is stopped and the whole is kept for one night in an atmosphere of hydrogen. The catalyst is filtered off, and the remainder is evaporated to dryness under vacuum.

The residue is chromatographed on silica with a 2:2:1 methanol/chloroform/ammonia mixture, and 115 mg of expected product are obtained.

The product is purified by passing it over an ion exchange resin of the carboxylic type in $NH_4^+$ form (elution with 0.5 N ammonia). The purification yield is 82.2%.

NMR spectrum. (in $D_2O$).

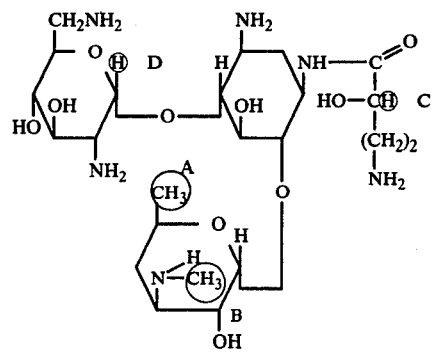

A - $CH_3$ - 1.2 ppm doublet J = 6 cps
B - $CH_3$ - 2.54 ppm
C - H - 4.28 ppm multiplet
D - H anomer 5.25 ppm doublet J = 4 cps

EXAMPLE 2

$N_1$ [L (−) 2-hydroxy 4-amino butyroyl/ 4-0-(2',6'-diamino 2',6'-didesoxy α, D glucopyranosyl] 6-0-[3"-methylamino 3",4",6"-tridesoxy α, D-xylohexopyranosyl] 2 desoxystreptamine sulfate.

1.8 grams of $N_1$ [L (−) 2-hydroxy 4-amino butyroyl/4-0-(2',6'-diamino 2',6'-didesoxy α, D glucopyranosyl] 6-0-[3"-methylamine 3",4",6" tridesoxy α, D-xylobexopyranosyl] 2-desoxystreptamine as prepared in Example 1 are dissolved in 120 cm³ of distilled water. The solution is acidified to a pH of 2 by the addition of 13.5 cm³ of normal sulfuric acid with a buret. The solution is concentrated to 20 cm³ and filtered on fritted glass. The solution is again concentrated to 10 cm³ and then 200 cm³ of methanol are added. The white suspension obtained was conserved under refrigeration for twenty hours and then filtered on fritted glass. The white crystals obtained were rinsed in methanol, then dried under reduced pressure. 1.87 g of the product were obtained. The mother liquor was evaporated to dryness and a second portion of product was obtained which weighed 0.35 g./$α/_D^{20}$ = 76.5° + 2.5° (c = 0.6% in water).

EXAMPLE 3

A preparation for injection was made up having the formula:

Product described in example 1 — 50 mg
Sterile aqueous excipient — 1 cm³

EXAMPLE 4

A preparation for injection was made up having the formula:

Product described in example 2 — 50 mg
Sterile aqueous excipient — 1cm3

Pharmacological studies of the product of formula I
Antibacterial activity in vitro: The antibacterial activity was measured in vitro by the method of diluting in liquid medium.

A series of tubes was prepared, in which the same amount of nutrient medium was apportioned. Increasing amounts of the antibiotic studied were distributed, then each tube was inoculated with a bacterial strain. After incubation for 18, 24 or 48 hours in the incubator at 37° C., the inhibition of the bacterial growth was estimated by transillumination, which enabled the minimum inhibiting concentrations (MIC) of the product, expressed here in μg/cm³ (as base), to be determined.
The results are shown in the following tables:

In vitro antibacterial activity:
The sulfate of formula I was tested in accordance A) Test on strains sensitive to aminoglycosides

|  | Product of formula I | | | Product of formula II | | Sulfate of the product of formula II | |
|---|---|---|---|---|---|---|---|
|  | 18 hours | 24 hours | 48 hours | 24 hours | 48 hours | 24 hours | 48 hours |
| *Staphylococcus Oxford* UC 1061 | 1 | 1 | 2 | 0.2 | 0.2 | 0.5 | 0.5 |
| + 5% human albumin | 2 | 5 | 10 | 0.6 | 0.6 |  |  |
| + 10% foal serum | 2 | 5 | 5 | 2 | 2 |  |  |
| *Staphylococcus Aureus* UC 1128 | 0.2 | 0.5 | 3 | 0.4 | 1 | 0.2 | 0.5 |
| + 5% human albumin | 3 | 5 | 20 | 0.4 | 2 |  |  |
| + 10% foal serum | 3 | 3 | 5 | 0.4 | 1 |  |  |
| *Streptococcus haemoliticus* | 1 | 1.5 | 1.5 | >40 |  | 40 | 100 |
| *Streptococcus faecalis* | 40 | 40 | >40 | >40 |  | >100 |  |
| *Escherichia Coli* UC 1020 | 3 | 3 | 5 | 0.6 | 1 | 1 | 1 |
| *Escherichia Coli* UC 1261 | 1 | 10 | 10 | 0.6 | 0.8 | 0.5 | 0.5 |
| *Klebsiella Pneumoniae* 52145 | 0.2 | 0.5 | 0.5 | 0.1 | 0.1 | 0.2 | 0.2 |
| Proteus (indol-) A 235 | 5 | 10 | 10 | 1 | 2 |  |  |
| *Pseudomonas pyocyanea* 3935 | 3 | 10 | 20 | >40 | >40 | >100 |  |
| *Salmonella typhimurium* 420 | 20 | 40 | >100 | 5 | 20 |  |  |

B) Test on strains resistant to gentamicine and/or tobramycine

|  | Product of Formula I | | | Product of Formula II | | | Sulfate of the Product of formula II | | |
|---|---|---|---|---|---|---|---|---|---|
|  | 18 hours | 24 hours | 48 hours | 18 hours | 24 hours | 48 hours | 18 hours | 24 hours | 48 hours |
| *Pseudomonas aeruginosa* DU 17 | 2 | 2 | 5 | >100 |  |  |  |  |  |
| *Pseudomonas aeruginosa* DU 1244 | 3 | 10 | 20 | >100 |  |  |  |  |  |
| *Pseudomonas aeruginosa* DU 8951 | 20 | 20 | 100 | >100 |  |  |  |  |  |
| *Klebsiella oxytoca* DU 14 | 1 | 1 | 2 | 10 | 20 | 20 |  |  |  |
| Providencia DU 48 | 20 | 40 | 40 | >100 |  |  |  |  |  |
| Providencia DU 49 | 40 | 40 | 40 | >100 |  |  |  |  |  |
| *Escherichia Coli* LA 290/K 55 | 1 | 2 | 2 | 10 | 10 | 40 |  |  |  |
| *Escherichia Coli* R 135/123 D | 2 | 3 | 5 | 10 | 20 | 40 |  |  |  |
| *Proteus Vulgaris* DU 23 | 3 | 5 | 10 | >100 |  |  |  |  |  |
| *Providencia stuartii* no. 21210 | 3 | 5 | 10 |  |  |  | 10 | 20 | 20 |
| *Pseudomonas aeruginosa* 20717 | 1 | 1 | 3 |  |  |  | >40 |  |  |
| *Pseudomonas aeruginosa* 20601 | 2 | 2 | 5 |  |  |  | >40 |  |  |
| *Escherichia Coli* 20895 | 1 | 2 | 5 |  |  |  | 40 | >40 |  |
| *Escherichia Coli* 20732 | 0.5 | 0.5 | 0.5 |  |  |  | 20 | 40 | >40 |
| *Escherichia Coli* 20683 | 5 | 10 | 40 |  |  |  | >40 |  |  |
| *Proteus rettgeri* 21207 | 10 | 20 | 40 |  |  |  | >40 |  |  |
| Providencia 164 | 2 | 2 | 2 |  |  |  | 10 | 10 | 10 |
| *Escherichia Coli* 9291 | 1 | 1 | 2 |  |  |  | >40 |  |  |
| *Klebsiella pneumoniae* COC 235 | 1 | 1 | 1 |  |  |  | >40 |  |  |
| *Klebsiella pneumoniae* COC 236 | 0.5 | 1 | 1 |  |  |  | >40 |  |  |
| *Klebsiella pneumoniae* COC 248 | 1 | 1 | 1 |  |  |  | >40 |  |  |
| *Escherichia Coli* DU 276 | 1 | 2 | 2 |  |  |  |  |  |  |
| *Escherichia Coli* Co c275 | 2 | 3 | 20 |  |  |  |  |  |  |
| *Escherichia Coli* 9640 | 2 | 2 | 2 |  |  |  |  |  |  |
| *Klebsiella pneumoniae* DU 193 | 0.5 | 0.5 | 1 |  |  |  |  |  |  |
| *Klebsiella pneumoniae* Co c260 | 0.5 | 0.5 | 0.5 |  |  |  |  |  |  |
| *Klebsiella pneumoniae* Co c229 | 1 | 1 | 2 |  |  |  |  |  |  |
| *Enterobacter cloacae* Co 2 | 0.5 | 0.5 | 1 |  |  |  |  |  |  |
| *Enterobacter aerogenes* C 010 | 0.2 | 0.5 | 0.5 |  |  |  |  |  |  |
| *Streptococcus faecalis* 5433 | 10 | 10 | 30 |  |  |  |  |  |  |
| *Klebsiella pneumoniae* DU 212 | 1 | 1 | 1 |  |  |  |  |  |  |
| *Klebsiella pneumoniae* DU 214 | 0.4 | 0.4 | 0.4 |  |  |  |  |  |  |
| *Klebsiella pneumoniae* DU 223 | 0.4 | 1 | 5 |  |  |  |  |  |  |
| *Klebsiella pneumoniae* DU 220 | 1 | 1 | 1 |  |  |  |  |  |  |
| *Klebsiella pneumoniae* DU 217 | 1 | 1 | 1 |  |  |  |  |  |  |
| *Escherichia Coli* DU 302 | 0.4 | 1 | 1 |  |  |  |  |  |  |
| *Escherichia Coli* R/55/123 D | 0.4 | 1 | 1 |  |  |  |  |  |  |
| Serratia Co B 35 | 3 | 5 | 5 |  |  |  |  |  |  |
| Serratia Co B 136 | 2 | 3 | 3 |  |  |  |  |  |  |

These results show that the product of formula I displays good activity against Gram-positive and Gram-negative microorganisms, more particularly marked against the latter.

This activity is particularly interesting against certain strains resistant to the aminoglycosides.

The product of formula II as well as its sulphate already possess good antibiotic activity.

The product of formula I possesses activity which is greatly increased with respect to these two products, in particular against certain microorganisms which are usually resistant to the aminoglycosides.

The increase in activity is particularly important against certain strains of Pseudomonas, Proteus and Klebsiella.

Pharmacological studies of the sulfate of formula I as prepared in example 2 were also carried out as follows:

with the procedure used for the product described in example 1.

The results are shown in the following table:

|  |  | C. M. I. en μg/cm³ | | |
|---|---|---|---|---|
|  |  | 18 H | 24 H | 48 H |
| *Staphylococcus aureus* | Medium | 0,4 | 0,6 | 1 |
|  | + 5% human albumin | 0,6 | 1 | 5 |
| ATCC 5638 Pen. Sensitive | +10% foal serum | 0,6 | 1,5 | 2 |
| *Staphylococcus aureus* | Medium | 0,6 | 0,6 | 1 |
|  | + 5% human albumin | 0,6 | 2 | 10 |
| UC 1128 Pen. Resistant | + 10% foal serum | 1 | 2 | 5 |
| *Staphylococcus aureus* Exp. n° 54146 | | 0,2 | 0,4 | 0,6 |
| *Staphylococcus aureus* Co 15 R cephalexin | | 5 | 10 | 40 |
| *Streptococcus pyogenes* A 561 | | 0,4 | 0,4 | 0,6 |
| *Streptococcus faecalis* 5432 | | 5 | 5 | 10 |
| *Streptococcus faecalis* 99 F 74 | | 2 | 5 | 15 |

|  | C. M. I. en μg/cm³ | | |
| --- | --- | --- | --- |
|  | 18 H | 24 H | 48 H |
| *Bacillus subtilis* ATCC 6633 | 0,05 | 0,05 | 0,1 |
| *Escherichia Coli* Tetracycline Sensitive ATCC 9637 | 2<br>2 | 5<br>5 | 20<br>20 |
| *Escherichia Coli* Tetracycline Resistant ATCC 11303 | 0,6 | 1 | 1 |
| *Escherichia Coli* Exp. T O₂₆B₆ | 1 | 1 | 2 |
| *Escherichia Coli* Gentamicin Resistant R 55 123 D | 0,4 | 0,4 | 2 |
| *Klebsiella pneumoniae* Exp. 52 145 | 0,2 | 0,2 | 0,4 |
| *Klebsiella pneumoniae* 2536 Gentamicin Resistant | 0,4 | 0,4 | 0,6 |
| *Proteus mit.* (indol—) A 235 | 2 | 5 | 5 |
| *Proteus vulgaris* (indol +) A 232 | 2 | 5 | 10 |
| *Salmonella thyphi* murium 420 | 2 | 5 | 20 |
| *Enterobacter cloacae* 681 | 0,2 | 0,4 | 0,4 |
| *Providencia* Du 48 | 10 | 20 | 40 |
| *Pseudomonas* 3935 Exp. Gentamicin Sensitivie | 2 | 5 | 10 |
| *Serratia* 2532 Gentamicin Resistant | 2 | 2 | 5 |

Experimental infection with *Escherichia coli*

A study of the action of the sulfate of example 2 on an experimental infection of mice with Escherishia Coli was conducted. An intraperitoneal injection with 0.5 cm³ of a 24 hour culture of a strain of *Escherichia coli* H.G. in nutritive broth diluted to 1/6 with distilled water is conducted on batches of 10 male mice.

Treatment is performed by the subcutaneous administration of the product of example 2 in the amounts designated in the table, 1, 5 and 24 hours after the above injection. The mortality rate was measured during 8 days, as well as the number of mice surviving after 8 days.

| POSOLOGY (total dosage) | MORTALITY AFTER | | | | | | | Mice Surviving to the Eighth Day |
| --- | --- | --- | --- | --- | --- | --- | --- | --- |
|  | 4 H 15 | 23 H 30 | 25 H 30 | 28 H 15 | 31 H 30 | 46 H | 94 H |  |
| CONTROL | 10 |  |  |  |  |  |  | 0/10 |
| 0,05 mg |  | 1 | 1 | 1 | 1 | 1 | 1 | 4/10 |
| 0,1 mg |  | 1 |  |  |  |  |  | 9/10 |
| 0,25 mg |  |  |  |  |  |  |  | 10/10 |

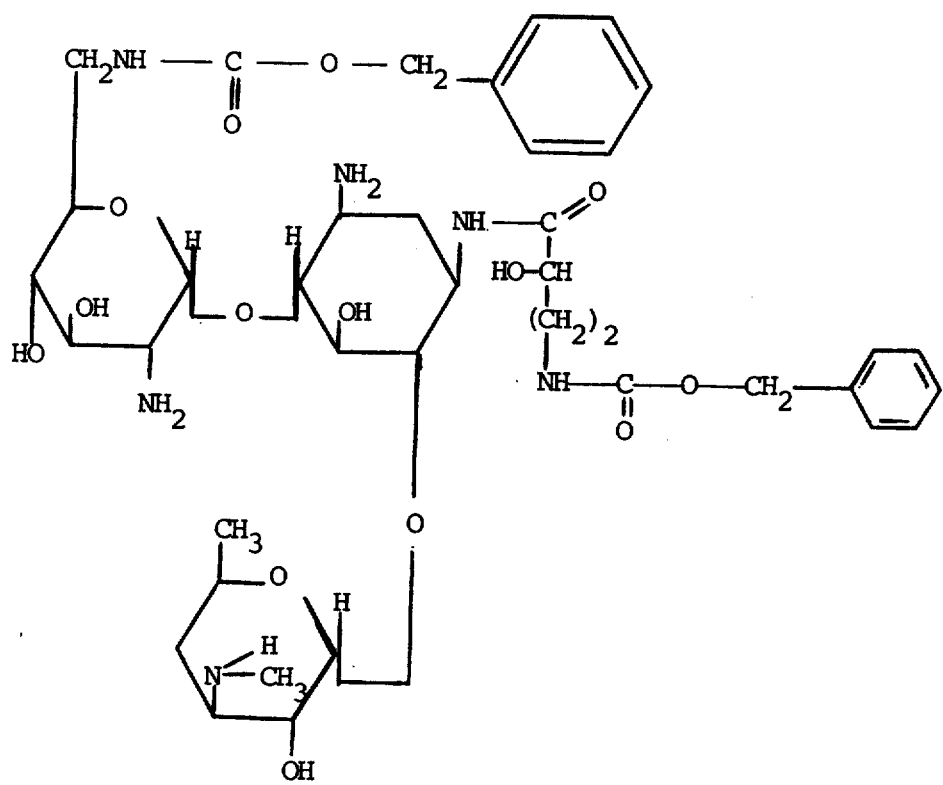

What is claimed is:

1. N₁ [L (—) 2-hydroxy 4-amino butyroyl] 4-0 [2',6'-diamino, 2', 6'-didesoxy α, D glucopyranosyl] 6-0 [3''-methylamino, 3'',4'',6''-tridesoxy α, D xylohexopyranosyl] 2-desoxy streptamine of the formula:

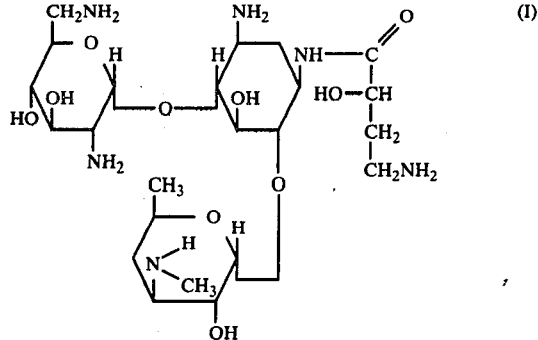

and pharmaceutically acceptable mineral and organic acid addition salts thereof.

2. The compound of claim 1 which is the hydrochloride, hydrobromide, nitrate, sulphate, phosphate, acetate, formate, benzoate, maleate, fumarate, succinate, tartrate, citrate, oxalate, benzylate, glyoxylate, aspartate, methanesulfonate or p-toluene-sulfonate thereof.

3. A pharmaceutical composition which comprises as an active principle the product of formula I of claim 1, or at least one of its therapeutically compatible salts and a pharmaceutically acceptable carrier.

4. A method for treating bacteria infections caused by staphylococcies, streptococcies, pneumonies, or colibacilloses, which comprises administering to a patient suffering from the infection an effective amount of the compound of claim 1.

5. A method for treating bacteria infections caused by Klebsiella, Pseudomonas or Enterobacter which comprises administering to a patient suffering from the infection an effective amount of the compound of claim 1.

6. The compound of claim 2 which is the sulfate.

7. A pharmaceutical composition which comprises as an active principle the product of claim 6 and a pharmaceutically acceptable carrier.

8. A method for treating bacteria infections caused by staphylococcies, streptococcies, pneumonies, or colibacilloses, which comprises administering to a patient suffering from the infection an effective amount of the compound of claim 6.

9. A method for treating bacteria infections caused by Klebsiella, Pseudomonas or Enterobacter which comprises administering to a patient suffering from the infection an effective amount of the compound of claim 6.

* * * * *

UNITED STATES PATENT AND TRADEMARK OFFICE
CERTIFICATE OF CORRECTION

PATENT NO. : 4,146,617  Page 1 of 2
DATED : March 27, 1979
INVENTOR(S) : Jean-Bernard Chazan et al.

It is certified that error appears in the above—identified patent and that said Letters Patent is hereby corrected as shown below:

Column 2, formula IV should appear as shown on the attached sheet.

Signed and Sealed this

Fourth Day of March 1980

[SEAL]

Attest:

SIDNEY A. DIAMOND

Attesting Officer   Commissioner of Patents and Trademarks